(12) United States Patent
Martínez Abán et al.

(10) Patent No.: US 9,727,690 B2
(45) Date of Patent: Aug. 8, 2017

(54) METHOD AND SYSTEM FOR MOLECULAR DYNAMICS SIMULATION WITH STABILITY CONTROL

(71) Applicant: PLEBIOTIC, S.L., Madrid (ES)

(72) Inventors: Roldán Martínez Abán, Madrid (ES); Pablo Echenique Robba, Madrid (ES); Javier Sancho Sanz, Madrid (ES); Roberto Martínez Benito, Madrid (ES); Alfonso Campo Camacho, Madrid (ES); Álvaro López Medrano, Madrid (ES)

(73) Assignee: PLEBIOTIC, S.L., Madrid (ES)

( * ) Notice: Subject to any disclaimer, the term of this patent is extended or adjusted under 35 U.S.C. 154(b) by 240 days.

(21) Appl. No.: 14/417,253

(22) PCT Filed: Dec. 21, 2012

(86) PCT No.: PCT/ES2012/070899
§ 371 (c)(1),
(2) Date: Jan. 26, 2015

(87) PCT Pub. No.: WO2014/016447
PCT Pub. Date: Jan. 30, 2014

(65) Prior Publication Data
US 2015/0278432 A1    Oct. 1, 2015

(30) Foreign Application Priority Data
Jul. 25, 2012  (ES) .................................. 201231189

(51) Int. Cl.
| | | |
|---|---|---|
| *G01N 33/48* | (2006.01) |
| *G01N 33/50* | (2006.01) |
| *G06F 19/12* | (2011.01) |
| *G06F 19/00* | (2011.01) |
| *G06F 19/16* | (2011.01) |

(52) U.S. Cl.
CPC ............ *G06F 19/12* (2013.01); *G06F 19/701* (2013.01); *G06F 19/706* (2013.01); *G06F 19/16* (2013.01)

(58) Field of Classification Search
None
See application file for complete search history.

(56) References Cited

U.S. PATENT DOCUMENTS

| | | |
|---|---|---|
| 1,005,325 A | 10/1911 | Scharf |
| 2,003,014 A | 5/1935 | Siegrist |
| 2003/0187626 A1 | 10/2003 | Catto |
| 2007/0239809 A1 | 10/2007 | Mosler |

FOREIGN PATENT DOCUMENTS

WO    0167310 A1    9/2001

OTHER PUBLICATIONS

Brooks et al. CHARMM: A program for macromolecular energy, minimization, and dynamics calculations. Journal of Computational Chemistry, vol. 4, 1983, pp. 187-217.*
International Search Report for corresponding application PCT/ES2012/070899 filed Dec. 21, 2012; Mail date Nov. 6, 2013.

* cited by examiner

*Primary Examiner* — Russell S Negin
(74) *Attorney, Agent, or Firm* — Cantor Colburn LLP

(57) ABSTRACT

The present invention is applicable in the field of molecular dynamics, said invention consisting of computing methods for predicting the structure and function of biomolecules, and particularly of proteins, by means of simulating the protein folding process and the interaction process of proteins with other biomolecules in a solvent. More particularly, the invention relates to a method and a system for controlling simulation stability and for choosing the timestep used in the numerical integration of the equations of motion. The invention successfully reduces the molecular dynamics simulation time by means of optimizing the timestep choice through an adaptive control or allowing larger timesteps correcting the trajectories based on a power control.

12 Claims, 6 Drawing Sheets

METHOD AND SYSTEM FOR MOLECULAR DYNAMICS SIMULATION WITH STABILITY CONTROL

TECHNICAL FIELD

The present invention is applicable in the field of molecular dynamics, said present invention consisting of computing methods for predicting the structure and function of biomolecules, and particularly of proteins, by means of simulating the protein folding process and the interaction process of proteins with other biomolecules in a solvent. Molecular dynamics also allow simulating simpler systems, such as gases or fluids, the present invention also being applicable. More particularly, the invention described herein relates, in molecular dynamics, to a method for controlling simulation stability and for choosing the timestep used in the numerical integration of the equations of motion.

The method of the invention is implemented in a computer or any suitable programmable electronic equipment, and provides the effect or advantage of reducing molecular dynamics simulation time by means of optimizing the timestep choice through an adaptive control or allowing larger timesteps correcting the trajectories based on a power control.

BACKGROUND OF THE INVENTION

The three-dimensional structure of a protein determines its biological function (see Berg J M, Tymoczko J L, Shyer L., *Biochemistry*, 5th edition, W H Freeman, 2002). Therefore, determining said structure is of vital importance for designing drugs, among others.

One way of determining the mentioned structure is by means of X-ray crystallization or nuclear magnetic resonance techniques (see P. Narayanan, *Essentials of Biophysics*, Second Edition, Anshan Ltd., 2010). Nevertheless, these techniques are not without imperfections and do not allow easily performing the opposite process, i.e., determining the amino acid chain which allows obtaining a certain structure (see Tamar Schlick, *Molecular Modeling and Simulation: An Interdisciplinary Guide*, Springer, 2006). These facts, along with increased computer processing capacity, have favored the development of molecular dynamics which consists of simulating the protein folding process or the interaction process of proteins with other molecules using a computer in recent years.

It has been demonstrated (see P. L. Freddolino, K. Schulten, *Common Structural Transitions in Explicit-Solvent Simulations of Villin Headpiece Folding*, Biophysical Journal Volume 97 October 2009 2338-2347, P. L. Freddolino, F. Liu, M. Gruebele, K. Schulten, *Ten-Microsecond Molecular Dynamics Simulation of a Fast-Folding WW Domain*, Biophysical Journal, Volume 94, Issue 10, L75-L77, 15 May 2008, S. K. Sadiq, G. De Fabritiis, *Explicit solvent dynamics and energetics of HIV-1 protease flap-opening and closing*, Proteins: Structure, Function, and Bioinformatics Volume 78, Issue 14, pages 2873-2885, 1 Nov. 2010) that approximation by means of Newton's mechanics is valid for modeling the dynamics (folding process or interaction process with other molecules) of large molecules such as proteins, which is known as molecular dynamics. Thus, by taking into account Newton's second law and that, in that case each atom is considered as a body of mass m, the equation determining the acceleration $\vec{a}$ to which the latter is subjected due to the existence of forces $\vec{F}_i$ between the latter and the other atoms of the actual protein or of the solvent, is the following:

$$\sum_{i=1}^{N} \vec{F}_i = m \cdot \vec{a} \quad (1)$$

N being the number of atoms.

The acceleration $\vec{a}$ to which a body is subjected is the derivative of the body velocity $\vec{v}$ over time. Therefore, said velocity can be obtained from integrating the mentioned acceleration $\vec{a}$ over time. Likewise, the position $\vec{x}$ is obtained as the integral of the velocity $\vec{v}$ over time given that the velocity is the derivative of position. Therefore, the position of each atom can be obtained by means of integrating from velocity and the latter is in turn obtained by means of integrating the acceleration which, with the forces acting on said atom known, provides the preceding equation 1.

Likewise, to simulate the actual conditions of proteins and of biomolecules in general, the molecule is surrounded with a solvent, water, simulating cell conditions. This solvent is necessary for certain biological processes such as protein folding, where the hydrophilic or hydrophobic nature is key for determining its structure.

This requires simulating, in addition to the protein under study, thousands of water molecules simulating the solvent, so the systems under study have thousands of atoms to be simulated.

For similar reasons, the so-called periodic boundary conditions are introduced to simulate experimental conditions of macroscopic systems (see T. Schlick, *Molecular Modeling and Simulation: An Interdisciplinary Guide*, Interdisciplinary Applied Mathematics series, vol. 21. Springer: New York, pp. 272-6. 2002). The system (the most solvent biomolecules) to be simulated is surrounded with periodic copies of itself in 3 directions.

This is a computationally approachable way for simulating the conditions of systems having a high number of molecules (of the order of Avogadro's number).

An efficient way of calculating the force acting on an atom due to its interaction with these copies is the so-called Particle Mesh Ewald (T. Darden, D. M. York, L. G. Pedersen, *Particle mesh Ewald: An N log(N) method for Ewald sums in large Systems, J. Chem. Phys.* (Communication) 98, 10089-10092 (1993)).

Before going into detail about the different types of force and the problem they entail, it is convenient to mention the basis of molecular dynamics, the solution of Newton's Second Law, equation 1.

It is a second-order differential equation with respect to the position and is therefore solved by integration.

This equation is equivalent to a first-order system of equations called Hamilton's equations, in what is called Hamiltonian formalism (see B. Leimkuhler, S. Reich, *Simulating Hamiltonian Dynamics*, Cambridge University Press 2004). Given that these solutions cannot be solved analytically in cases such as molecular dynamics, a numerical solution of said differential equations is necessary.

Said solution, called numerical integration, is based on going from a continuous time to a discrete time. The gap between each of the discrete time instants is called a timestep. Starting from initial position and velocity conditions, the values thereof in the entire subsequent instants are to be found. The function which allows obtaining a value for the following instant from the position and velocity value in one instant is called an integrator. Therefore, the integrator and the timestep determine simulation quality.

Given that an approximation is performed when going from a continuous time to a discrete time, the greater the timestep, the worse the solution of the differential equation.

If an excessively large timestep is chosen, the solution obtained may have nothing to do with the actual solution and it may diverge from it. In that case, the integrator is said to be unstable for that timestep. The range of timestep values for which an integrator is stable is called a stability zone (see E. Hairer, S. P. Nørsett, Gerhard Wanner, *Solving ordinary differential equations I: Nonstiff problems*, second edition, Springer Verlag, Berlin, 1993). The forces $\vec{F}_i$ to which each atom is subjected are of a different nature in terms of their magnitude, their variability over time and are the function of the position of the remaining atoms of the protein or of the atoms of the solvent.

The aforementioned numerical integration process is based on gradually moving the simulation forward at time intervals until reaching the end time thereof. Due to the very high frequency (variability over time) of some of the forces $\vec{F}_i$, these time intervals are very small, of the order of femtoseconds ($10^{-15}$ seconds). The total simulation times required for simulating a complete protein folding, for example, range from microseconds to several minutes (David Sheehan, *Physical Biochemistry*, Second Edition, John Wiley & Sons, 2009), therefore the number of time intervals necessary for completing the simulation range from $10^{10}$ to $10^{16}$. In each of these time intervals, it is necessary to perform complex computational calculations, mainly those corresponding to the forces $\vec{F}_i$, and furthermore, these calculations increase exponentially with the complexity of the system. This means that even the most powerful computers today need a very long computing time of the order of days, months and even years to complete the simulation of medium-sized molecular systems (see Tamar Schlick, *Molecular Modeling and Simulation: An Interdisciplinary Guide*, Springer, 2006. J. C. Phillips, R. Braun, W. Wang, J. Gumbart, E. Tajkhorshid, E. Villa, C. Chypot, R. D. Skeel, L. Kale, K. Schulten, *Scalable molecular dynamics with NAMD*, Journal of Computational Chemistry, 26:1781-1802, 2005).

It is easily deduced from this that the techniques known in the state of the art in molecular dynamics have the technical problem that they do not allow performing simulations with the speed demanded by pharmaceutical industry or research organizations.

Among the mentioned $\vec{F}_i$, the binding forces model very high frequency vibrations and therefore really need very small time intervals for being integrated: from 1 to 10 femtoseconds. In contrast, among these forces $\vec{F}_i$ there are other forces such as Van Der Waals or electrostatic forces (Tamar Schlick, *Molecular Modeling and Simulation: An Interdisciplinary Guide*, Springer, 2006) which, compared with the previous binding forces, are long-range forces having a much smaller frequency, and for which, in principle, much greater time intervals (of the order of two orders of magnitude more than those corresponding to binding forces) may be sufficient for being integrated. It must be highlighted that compared with binding forces which only take into account the interactions between one atom and its closest neighbor, these long-range forces have a very high computing cost since they involve the interactions of one atom with the other atoms of the protein or molecule, as well as with the atoms of the solvent. Therefore, while the evaluation of such forces has a complexity of O(N), for some the complexity is O($N^2$) (Tamar Schlick, *Molecular Modeling and Simulation: An Interdisciplinary Guide*, Springer, 2006).

Due to its simplicity and exceptional stability in long-term simulations such as those required in molecular dynamics, the integrator is the Leapfrog/Verlet/Stormer method (see L. Verlet, *Computer 'experiment' on classical fluids: I. Thermodynamical properties of Lennard-Jones molecules*, Phys. Rev., 159 (1):98-103, July 1967), commonly known in short as the Verlet method. It is an explicit, second-order integrator with the particularity that it only requires evaluating the forces once every iteration, whereas other integrators of the same order (e.g., second-order Runge Kutta) require 2 evaluations, and therefore virtually twice the computing cost.

Like the differential equations that it attempts to integrate, Verlet, as a numerical integrator, has important mathematical properties such as symplecticity and time symmetry. Therefore it more faithfully represents the system that it is simulating, maintaining certain physical properties such as energy conservation and time reversibility, and mathematical properties such as physical volume conservation, which will result in a greater stability. There are variants of this method such as the velocity Verlet or the position Verlet which are widely used and which also have these important properties.

Using symplectic integrators is common in various fields of mechanics (see B. Gladman, M. Duncan, J. Candy, *Symplectic integrators for long-term integrations in celestial mechanics*, Celest. Mech. Dynam. Astron., 52, 221-240 1991) due to the discovery of their greater efficiency with respect to non-symplectic integrators (see M. P. Calvo, J. M. Sanz-Serna, *The development of variable-step symplectic integrators, with application to the two-body problem*, SIAM J. Sci. Comput., 14, 936-952. 1993). The use of a variable timestep for a symplectic integrator is also known to reduce its efficiency (R. D. Skeel, C. W. Gear, *Does variable step size ruin a symplectic integrator?* Physica D, 60, 311-313. 1992) and its stability (see R. D. Skeel, *Variable step size destabilizes the Störmer/leapfrog/Verlet method*, BIT, 33, 172-175. 1993).

Due to the complexity and therefore the chaotic behavior of the systems simulated in molecular dynamics, with thousands of degrees of freedom, the tracking of a particular atom is not relevant. One characteristic of chaotic systems is their sensitivity to initial conditions, such that a small variation in one of the dynamic variables leads to a completely different trajectory. In a molecular system there is always an initial inaccuracy in the initial positions and velocities of the system due to temperature and to problems of measuring the positions of the atoms, so a particular trajectory will be not representative. However, statistical variables as well as the configurations corresponding to local minima of the energy, which will be the conformations that the trajectories are inclined to have, are of interest. In the case of a protein, it will correspond to its native state.

Therefore, in molecular dynamics high precision in the trajectories is not necessary, which allows using non-symplectic integrators and using a variable timestep for improving efficiency (see S. J. Stuart, J. M. Hicks, M. T. Mury, *An Iterative Variable-timestep Algorithm for Molecular Dynamics Simulations*, Molecular Simulation, Volume 29, Issue 3 2003, pages 177-186).

Both the aforementioned techniques and those which will be described below of imposing restrictions on the high-frequency components of binding forces, and the techniques based on increasing the interval of integration of slow forces, are modifications or variations of the mentioned Leapfrog/Verlet/Stormer method.

Among the techniques of imposing restrictions (constraints) for damping high frequencies include those known as SHAKE (see J. P. Ryckaert, G. Ciccotti and H. J. C. Berendsen, *Numerical integration of the Cartesian equations of motion of a system with constraints: Molecular dynamics of n-alkanes*, J. Comput. Phys., 23:327-341, 1977). RATTLE (see H. C. Andersen. *Rattle: a 'velocity' version of the SHAKE algorithm for molecular dynamics calculations*, J. Comput. Phys., 52:24-34, 1983.) and WIGGLE (Lee, Sang-Ho, K. Palmo, S. Krimm (2005). WIGGLE: *A new constrained molecular dynamics algorithm in Cartesian coordinates*, Journal of Computational Physics 210: 171-182 2005). Both techniques are combined with the Verlet method or with one of the mentioned variants. Nevertheless, the success thereof in terms of increasing the interval of integration has been rather limited and have only provided factors of acceleration of between 2 and 5 (see Michael A. Sherman et al., *Method for large timesteps in molecular modeling*, U.S. patent Ser. No. 10/053,253), a completely insufficient improvement given the very long computing times provided, as mentioned, by the state of the art in molecular dynamics.

The most well known technique based on increasing the interval of integration of slow forces is known as MTS (multiple-timestep). In them, the conventional methods of integration in molecular dynamics (Verlet and its variants) are modified by evaluating the slow forces less frequently than the fast forces. The most popular and by far the most widespread MTS method in commercial simulators (GROMACS: H. J. C. Berendsen, D. van der Spoel and R. van Drunen, GROMACS: *A message-passing parallel molecular dynamics implementation*, Computer Physics Communications Volume 91, Issues 1-3, 2 Sep. 1995, Pages 43-56, AMBER: D. A. Pearlman, D. A. Case, J. W. Caldwell, W. S. Ross, T. E. Cheatham, S. DeBolt, D. Ferguson, G. Seibel, P. Kollman, *AMBER, a package of computer programs for applying molecular mechanics, normal mode analysis, molecular dynamics and free energy calculations to simulate the structural and energetic properties of molecules*, Computer Physics Communications Volume 91, Issues 1-3, 2 Sep. 1995, Pages 1-41, CHARMM: B. R. Brooks, R. E. Bruccoleri, B. D. Olafson, D. J. States, S. Swaminathan, M. Karplus, *CHARMM: A program for macromolecular energy, minimization, and dynamics calculations*, Journal of Computational Chemistry Volume 4, Issue 2, pages 187-217, Summer 1983, NAMD: J. C. Phillips, R. Braun, W. Wang, J. Gumbart, E. Tajkhorshid, E. Villa, C. Chypot, R. D. Skeel, L. Kale, K. Schulten, *Scalable molecular dynamics with NAMD*, Journal of Computational Chemistry, 26:1781-1802, 2005,) is that known as r-Respa (M. E. Tuckerman, B. J. Berne, and G. J. Martyna, *Reversible multiple time scale molecular dynamics*. J. Chem. Phys., 97:1990-2001, 1992.), also called Verlet-I (see H. Grubmüller, H. Heller, A. Windemuth, and K. Schulten, *Generalized Verlet algorithm for efficient molecular dynamics simulations with long-range interactions*, Mol. Sim., 6:121-142, 1991) and which was proposed independently in the two preceding references. The philosophy of the r-Respa method is common for MTS methods, i.e., the less frequent evaluation of the fast forces, such that in each of these evaluations, the magnitude of the force which has not been taken into account between said evaluations is accumulated, these forces are thus updated by impulses. The improvement in the step of r-Respa integration is again marginal with typical times ranging from 0.5 fs, 2 fs, 4 fs (see H. Grubmüller, P. Tavan, *Multiple Timestep Algorithms for Molecular Dynamics Simulations or f Proteins: How Good Are They?*, Journal of Computational Chemistry, Vol. 19, No. 13, 1998) to 1 fs, 2 fs and 5 fs (see T. C. Bishop, R. D. Skeel, K. Schulten, *Difficulties with Multiple Timestepping and Fast Multipole Algorithm in Molecular Dynamics*, Journal of Computational Chemistry, Vol. 18, No. 14, 1997) and therefore very far from what is really needed in molecular dynamics. The main reason for this marginal r-Respa improvement is that the update of the slow forces by means of impulses happens periodically, particularly at a frequency close to multiples of some of the natural frequencies of the system. This circumstance means that the system enters into resonance (Schlick, M. Mandziuk, R. D. Skeel, and K. Srinivas, *Nonlinear resonance artifacts in molecular dynamics simulations*, J. Comput. Phys., 139:1-29, 1998) and the simulation is therefore not viable.

To prevent these resonances the family of integrators, MOLLY, (see B. Garcia-Archilla, J. M. Sanz-Serna & R. D. Skeel, *Long-time-step methods for oscillatory differential equations*, SIAM J. Sci. Comput. 20(1998), 930-963 and also J. M. Sanz-Serna, *Mollified impulse methods for highly-oscillatory differential equations*, SIAM J. Numer. Anal. 46(2008), 1040-1059) was introduced. Despite being an alternative to the use of restrictions, the timestep continues to be restricted to a few femtoseconds, allowing only a 50% increase in the timestep (J. A. Izaguirre, Q. Ma, T. Matthey, J. Willcock, T. Slabach, B. Moore, G. Viamontes, *Overcoming instabilities in Verlet-I/r-RESPA with the mollified impulse method*).

An alternative is to increase the mass of the hydrogen atoms because, due to their low mass, their bonds with other atoms are responsible for the higher oscillation frequencies. These methods allow increasing the timestep for the fast forces up to 4 fs without altering the dynamics, in comparison with the 2 fs of MOLLY, and reach up to 7 fs at the expense of eliminating the fastest oscillations of the system, but without modifying the thermodynamic equilibrium properties of the system (see K. A. Feenstra, B. Hess, H. J. C. Berendsen, *Improving efficiency of large time-scale molecular dynamics simulations of hydrogen-rich Systems*, Journal of Comput. Chem. Volume 20, Issue 8, pages 786-798, June 1999)

The molecular dynamics model will be seen below.

The basic unit of this model is the atom. A potential modeling the interactions between atoms is introduced for a system of N atoms.

The reason for introducing a potential instead of directly introducing the forces is both physical, because the energy can be written as the kinetic energy plus said potential, and mathematical, because potential is a scalar function.

The force can be easily obtained from the potential by simply applying the gradient, therefore if $\vec{r}_1, \vec{r}_2, \ldots, \vec{r}_i, \ldots, \vec{r}_N$ are the coordinates of the N atoms, Newton's equation is written based on the potential $U_{TOTAL}$ as $$m_i \frac{d^2 \vec{r}_i}{dt^2} = -\frac{\partial}{\partial \vec{r}_i} U_{TOTAL}(\vec{r}_1, \vec{r}_2, \ldots, \vec{r}_N) \qquad (2)$$

Given the different types of occurring interactions, this potential is the sum of different contributions:

$$U_{TOTAL} = U_{BOND} + U_{ANGLE} + U_{DIHEDRAL} + U_{VDW} + U_{COULOMB} \qquad (3)$$

The more common analytical expressions thereof being the following $$U_{BOND} = \sum_{bonds} k_i^{bond}(r_i - r_{i0})^2 \quad (4)$$

$$U_{ANGLE} = \sum_{angles} k_i^{angle}(\theta_i - \theta_{i0})^2 \quad (5)$$

$$U_{DIHEDRAL} = \sum_{dihedrals} \sum_{n_i} k_i^{dihed}[1 + \cos(n_i \phi_i - \gamma_i)] \quad (6)$$

$$U_{VDW} = \sum_i \sum_{j>i} 4\varepsilon_{ij} \left[ \left( \frac{\sigma_{ij}}{r_{ij}} \right)^{12} - \left( \frac{\sigma_{ij}}{r_{ij}} \right)^6 \right] \quad (7)$$

$$U_{COULOMB} = \sum_i \sum_{j>i} \frac{q_j q_i}{4\pi\varepsilon_0 r_{ij}} \quad (8)$$

$U_{BOND}$ is called bond distance potential, $r_i$ being the distance at which the atoms forming the $i^{th}$ bond are located, $r_{i0}$ is the equilibrium distance for said bond, and $k_i^{bond}$ is a constant quantifying the force of said bond, particularly of the harmonic potential used. This potential and the force derived therefrom model the fact that bound atoms are at a certain distance with respect to one another. For example, the distance of two carbon atoms bound by a single bond is about 1.54 amstrongs, which would be the equilibrium distance for this molecular model $U_{ANGLE}$ is called bond angle potential, $\theta_i$ being formed by 3 bound atoms, $\theta_{i0}$ is the equilibrium angle for said angle, and $k_i^{angle}$ is a constant quantifying the magnitude of said force, and which is related to the force and characteristics of the binding forces between the 3 atoms forming the angle. It models the angle formed by bound atoms. For example, for a water molecule, the equilibrium angle for the angle formed by the oxygen atom and hydrogen atom is about 105°.

$U_{DIHEDRAL}$ is called torsion or dihedral angle potential, $\phi_i$ being the angle formed by the planes defined by four bound atoms, $\gamma_i$ is the equilibrium angle for said angle of torsion, $n_i$ is the so-called multiplicity, since given the periodic nature of this force various equilibrium angles can exist and $k_i^{dihed}$ is a constant quantifying said force. This potential models the planarity of certain molecules.

$U_{VDW}$ is the potential modeling the Van Der Waals type interactions between unbound atoms. The origin thereof is in the electromagnetic interactions between atoms due to the atomic structure, in this case the functional dependency is the so-called Lennard-Jones potential, where $r_{ij}$ is the distance between the $i^{th}$ and $j^{th}$ atoms, and $\epsilon_{ij}$ and $\sigma_{ij}$ are two constants quantifying the intensity of the interaction between that pair of atoms, having a long-range attraction nature and a very short-range repulsion nature.

$U_{COULOMB}$ is the Coulomb potential modeling the electrostatic interactions between unbound atoms, where $r_{ij}$ is the distance between the $i^{th}$ and $j^{th}$ atoms, $q_i$ and $q_j$ are their respective effective charges, and $\epsilon_0$ is the constant quantifying the intensity of the electrostatic force, called in this case the electric permittivity of the medium.

The various constants are obtained by semi-empirical means called force field constants (see J. W Ponder, D. A. Case, *Force fields for protein simulations*, Adv. Prot. Chem. 66 27-85 (2003)). They reflect the properties experimentally observed for the molecules. Given that the atomic bond and the atomic structure are governed by quantum mechanics, calculations based on quantum dynamics and on the experimental data are used for obtaining this Newtonian model of molecular dynamics.

Therefore, each force field tabulates the set of values necessary for modeling the molecule.

There are other possibilities for the functional dependency of the different potentials (see Chapter 8, Tamar Schlick, *Molecular Modeling and Simulation: An Interdisciplinary Guide*, Springer, 2006).

$U_{BOND}$, $U_{ANGLE}$, $U_{DIHEDRAL}$ model the molecule structure due to the atomic bond. The effect thereof is to provide the experimental value for the distances and the angles between bound atoms. Given the force of the covalent bond, they are fast forces with high frequency oscillations.

The fact that they are calculated as a summation with respect to the number of bonds, angles and dihedral angles (torsions), the number of which is approximately proportional to N, is what determines the O(N) dependency of the computing cost.

$U_{VDW}$ and $U_{COULOMB}$ in turn model the electromagnetic interactions between unbound atoms. The double summation is caused by the $O(N^2)$ dependency of the computing cost.

The effect of the periodic boundary conditions calculated by means of the aforementioned Particle Mesh Ewald method, providing an extra potential $U_{EWALD}$, must be added to these potentials For correct numerical integration of Newton's equation linking the coordinate variation with force and velocity, the rate of force variation is crucial.

This is because the greater the force variation between two time instants, the greater the numerical error.

A numerical integrator allows finding the coordinate value of the atoms in one instant based on a preceding instant, the time gap between both instants being the timestep h.

If the vector formed by the positions and velocities of the atoms of the system is called $\vec{q}_i$, the following will be true:

$$\vec{q}_{i+1} = \vec{I}(q_i, h) \quad (9)$$

$\vec{I}(\vec{q}_i, h)$ being the integrator. The coordinate dependency is essentially due to the force calculation, i.e., $$\vec{q}_{i+1} = \vec{I}(\vec{F}(\vec{q}_i), h) \quad (10)$$

Each integrator is characterized by a computing cost due to the force calculation FC and to the new coordinate calculation CC.

In the case of explicit integrators, this latter is significant. This is not the same for implicit integrators where this cost can be higher.

For good integration it is necessary that the force variation in interval h is small.

For the case of a variable timestep, predicting this variation is key in choosing the timestep.

For simulating the experimental conditions, the so-called thermostats (constant temperature) and barostats (constant pressure) are introduced, these conditions being present in actual systems. Berendsen's method (Berendsen, H. J. C.; Postma, J. P. M.; van Gunsteren, W. F.; DiNola, A.; Haak, J. R. (1984), *Molecular-Dynamics with Coupling to an External Bath*, Journal of Chemical Physics 81 (8): 3684-3690 (1984)), Nose-Hoover's method (see Nose, S, *A unified formulation of the constant temperature molecular-dynamics methods*, Journal of Chemical Physics 81 (1): 511-519 (1984) and also G J Martyna, D J Tobias, M L Klein, *Constant pressure molecular dynamics algorithms*, J. Chem. Phys 101(5), 1994) are commonly used, and the methods based on Langevin dynamics (see T. Schlick, *Molecular Modeling and Simulation*, Springer. pp. 435-438 (2002) and also S E Feller, Y. Zhang, R W Pastor and B R Brooks, *Constant pressure molecular dynamics simulation: The Langevin piston method*, J. Chem. Phys. 103(11), 1995) are particularly used. An integrator integrating Langevin dynamics is called a BBK integrator (see A. Brunger, C. L. Brooks, M. Karplus, *Stochastic boundary conditions for molecular dynamics simulations of ST2 water*, Chem. Phys. Lett., 105 (1984), pp. 495-500.)

The mentioned Langevin dynamics adds a stochastic term to Newton's equation, so energy is no longer conserved and the dynamics are not reversible, but it simulates the thermodynamic properties of a system at a constant temperature. A damping term proportional to velocity is further introduced. This term stabilizes the dynamics and allows increasing the timestep. However, in order for the dynamics to be realistic, the damping factor must not exceed a value, and the timestep reached must not exceed 14 fs for slow forces (see J. A. Izaguirre, D. P. Catarello, J. M. Wozniak, R. D. Skeel, *Langevin stabilization of molecular dynamics*, Journal of Chem. Phys. Volume 114 number 5 1 (2001)) or even 16 fs (see Q. Ma and J. A. Izaguirre, *Targeted mollified impulse—a multiscale stochastic integrator for long molecular dynamics simulations*). However, these methods use a high damping term which slows down the simulation, and therefore involves more iterations to reach the desired state, in addition to not reaching the timestep which would allow the dynamics of slow forces.

Despite recent computational advances which allow the millisecond simulation of a protein in a reasonable time (see D. E. Shaw, R. O. Dror, J. K. Salmon, J. P. Grossman, K. M. Mackenzie, J. A. Bank, C. Young, M. M. D., B. Batson, K. J. B., E. Chow, M. P. Eastwood, D. J. Ierardi, J. L. Klepeis, J. S. Kuskin, R. H. Larson, K. Lindorff-Larsen, P. Maragakis, M. A. Moraes, S. Piana, Y. Shan, B. Towles, *Millisecond-Scale Molecular Dynamics Simulations on Anton*, Proceedings of the Conference on High Performance Computing, Networking, Storage and Analysis (SC09), New York, N.Y.: ACM Press, 2009), these are based on solely computational improvements. They do not however overcome the femtosecond scale for the integration step, so there is still a need for enormous computational resources that are beyond the reach of many.

BRIEF SUMMARY OF THE INVENTION

The present invention solves the aforementioned problem by means of the subject matter defined in the attached independent claims.

This invention presents a method for efficiently simulating a system made up of atoms by means of molecular dynamics.

This simulation is based on the integration of Newton's Laws, for which the choice of the timestep required in the numerical integrator is crucial.

Given the complexity of these systems, the choice of the optimum timestep is not trivial.

These simulations are usually performed at a fixed timestep value small enough to assure a good integration. However, this value is not always the maximum value which could be used in the integration, whereby there is a loss of efficiency. The present invention is based on using a variable timestep which is adapted continuously to the dynamics of the system of atoms to be simulated, searching for the possible maximum value without compromising simulation stability.

To that end, the power of each atom is calculated in the method of the invention. The power of an atom will tell if an atom will be sped up or slowed down and by what magnitude. This provides information about the dynamic state of the system, in addition to allowing the prediction of its future behavior.

A first effect of knowing the dynamic state of the system at all times is to enable determining a timestep which is adapted to the dynamics thereof.

Furthermore, the predictive nature of this criterion, which is key for increasing gain, allows preventing the problems due to atoms that are going to be sped up excessively. To that end, reducing their velocity such that their power is in normal values is enough. Likewise, this criterion is applicable to dynamics using algorithms such as constraint algorithms, Langevin dynamics or algorithms with different timesteps for different forces (multistep) where other criteria are not easily applicable.

Therefore, a first aspect of the invention relates to a computer-implemented method for simulating systems of atoms by means of molecular dynamics, which comprises using at least one numerical integrator for integrating the equations of motion of the atoms of said system. The method further comprises controlling the power of at least part of the atoms of the system to be simulated by means of the adaptive modification of the timestep value of said numerical integrator, maintaining power within a stability range of power within which the simulation of the system is considered stable.

By means of said computer, the equations of motion of the atoms are integrated at the times marked by the timestep chosen for the integrator which, as a result of the power control maintaining the simulation stable, will be maximum without losing stability, which produces the effect that the number of integrations that has to be calculated by the computer is reduced and therefore the simulation is completed in less time.

The invention achieves the technical advantage or effect of performing complex molecular dynamics simulations with great speed, but by using computers with a conventional computing capacity.

Another aspect of the invention relates to a piece of equipment or a system for simulating systems of atoms by means of molecular dynamics, comprising at least one computer programmed for integrating the equations of motion of the atoms of the system by means of at least one numerical integrator. Said at least one computer is programmed for controlling the power of at least part of the atoms of the system to be simulated, adaptively modifying the timestep value of said numerical integrator, such that power is maintained within a stability range of power within which the simulation of the system is considered stable.

The computer comprises data input means, data output means, a processor and a computer program stored in the computer memory. Said program is preferably suitable for selecting drugs, and the system of atoms to be simulated corresponds with a biomolecule, such that said program generates an output datum about if the drug meets a pre-established criterion once run by said processor.

The program carries out a power control loop in which the power of at least part of the atoms of the system to be simulated is calculated, and the timestep of said numerical integrator is adaptively modified depending on the calculated power of the atoms, such that if the power is less than a lower threshold of the stability range, the timestep of the integrator is increased, and such that if the power is greater than an upper threshold of the stability range, the timestep of the integrator is reduced. By means of said computer, the equations of motion of the atoms are integrated at the times marked by the timestep chosen for the integrator in each instant. Therefore, the invention successfully optimizes the use of the computer processing capacity since it reduces the number of integrations which said computer has to calculate to complete the simulation, and therefore reducing the simulation time.

The invention applied to the field of drug design enables testing a greater amount of chemical compounds, and therefore increases the possibility of finding useful compounds for treating diseases.

The invention also relates to a computer program stored in a data carrier, the program being suitable for selecting drugs, such that it is capable of implementing the method of the invention when run in a computer.

PREFERRED EMBODIMENT OF THE INVENTION

Figure 1:
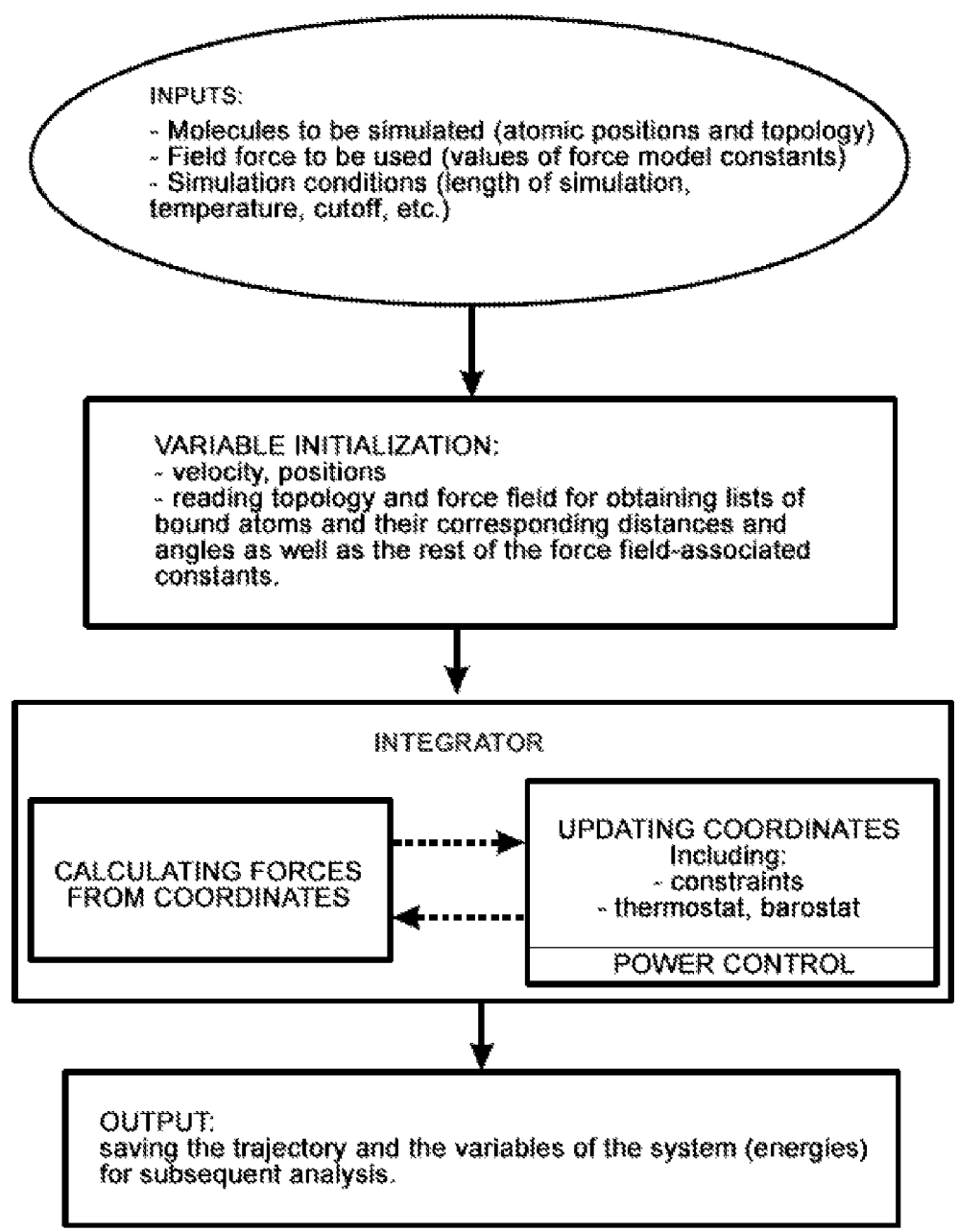
FIG. 1 shows a general diagram of the phases of a method for simulating molecular dynamics. The power control is performed when updating the coordinates (positions and velocities) of the integrator.

FIG. 1 shows the general scheme of a molecular dynamics simulator. The first step is to read the physical variables of the system to be simulated. These variables include the initial positions and velocities of the atoms to be simulated, the force field parameters for said atoms, the conditions to be simulated, for example temperature and pressure, and various configuration parameters for the system, such as the number of steps to be simulated and various internal configuration parameters of the program.

Said variables must be brought to the internal variables of the program.

The next part is the core of the simulator, the integrator, which as has been mentioned, is responsible for calculating the positions, velocities and forces of the atoms of the system for each step of the simulation. The present invention relates precisely to this part of the integrator, particularly to the part of updating the coordinates (positions and velocities), modifying the velocities or the timestep.

In a stable simulation, both total and individual power values are within a stability range of values which can be considered normal. Likewise, if the power values are within this stability range, the simulation is stable.

This allows controlling simulation stability, which is somewhat difficult a priori, based on controlling a parameter, the power of the atoms.

The invention successfully uses the maximum timestep possible, maintaining the simulation stable at all times, which can be achieved as mentioned, by maintaining the power within a range of values that can be called a stability range.

There are different possibilities to that end.

In each iteration i of the simulation corresponding to a discrete time instant, the state of each atom α is described by its position $\vec{r}_i^{\,\alpha}$ and velocity $\vec{v}_i^{\,\alpha}$. Based on the positions of each atom, the force $\vec{F}_i^{\,\alpha}$ and the acceleration $\vec{a}_i^{\,\alpha}$ acting thereon can be calculated.

The power $p_i^{\alpha}$ of the atom α in the instant i is defined as the scalar product of the velocity of an atom times the force to which it is subjected:

$$p_i^{\alpha} = \vec{F}_i^{\,\alpha} \cdot \vec{v}_i^{\,\alpha} \tag{11}$$

$p_i$ is defined as the largest of all the $p_i^{\alpha}$, i.e., the power value of the atom with the highest power.

In Newtonian dynamics, power is a measurement of kinetic energy variation for a particle, and therefore in this case, for an atom.

In the case of positive power, an atom gains kinetic energy, whereas in the case of negative power, an atom loses energy, the atom is damped.

Given that a numerical integration of Newton's equation is being performed, a good integration maintaining this physical property is anticipated.

The total power $P_i^{\alpha}$ can also be defined as the sum of the power $p_i^{\alpha}$ for all the N atoms of the system:

$$P_i = \sum_N p_i^{\alpha} \tag{12}$$

Likewise, power variation $\Delta p_i^{\alpha}$ can be defined as the power difference for an atom between two consecutive iterations:

$$\Delta p_i^{\alpha} = p_i^{\alpha} - p_{i-1}^{\alpha} \tag{13}$$

and $\Delta P_i$ can be defined as the total power variation between two iterations $$\Delta P_i = P_i - P_{i-1} \tag{14}$$

$\Delta p_i$ is defined as the largest of all the $\Delta p_i^{\alpha}$.

For these dynamic variables of the system, thresholds u, U, δ and Δ can be defined such that in good simulation conditions, the variables $p_i$, $P_i$, $\Delta p_i$, $\Delta P_i$ always have values less than the corresponding thresholds thereof.

This threshold will depend on two simulation characteristics:
the system to be simulated: both the force field used and the type of atoms of the system can affect these thresholds.
The size of the system also affects the total amounts
simulation conditions: the temperature, which is related to kinetic energy, will influence normal power values. The use of constraints will also have an effect since certain binding forces are eliminated. Likewise, more demand can be placed on the simulation quality, seeking good energy conservation, which involves a smaller timestep and also smaller power and therefore threshold values.

Figure 2:
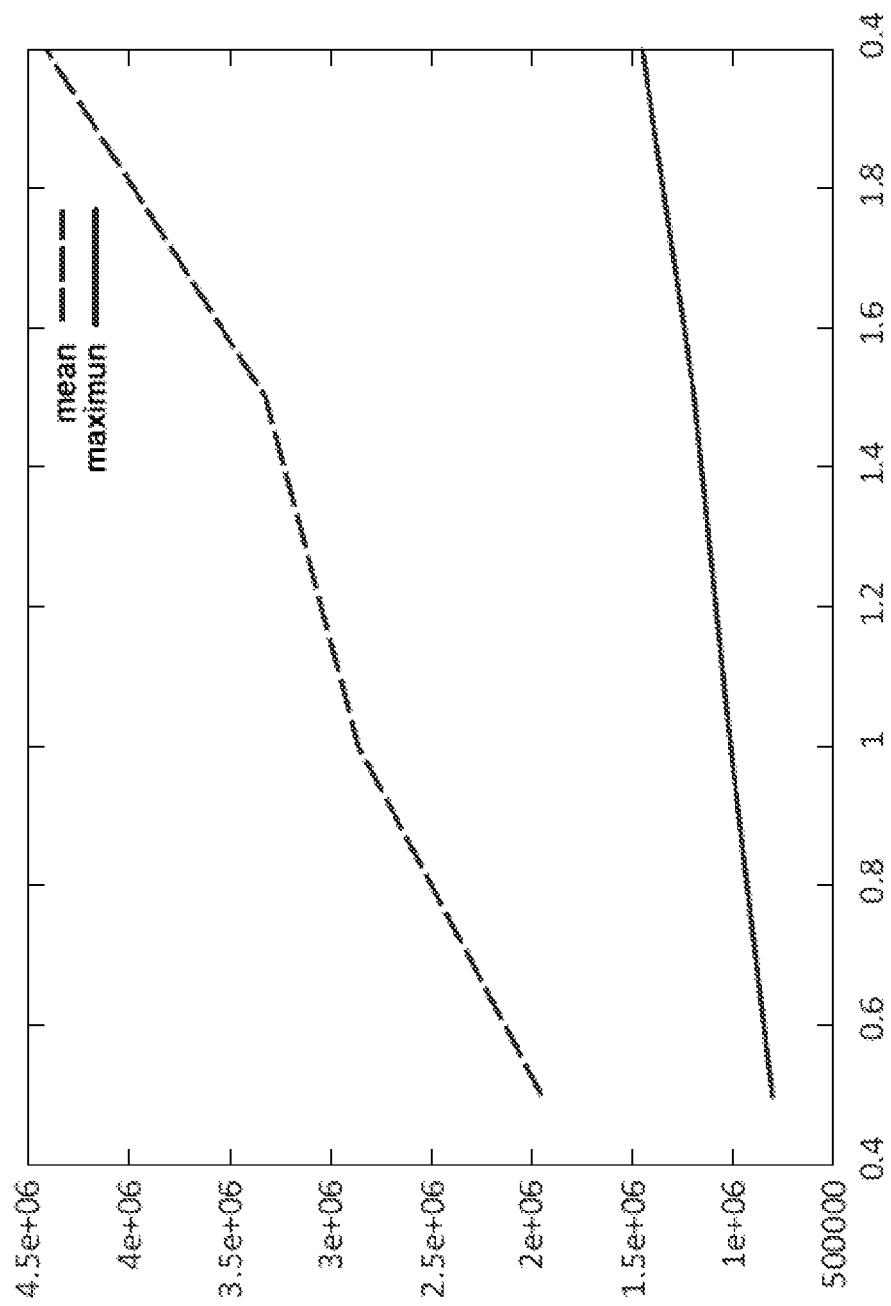
FIG. 2 shows a graph of the power dependency with respect to timestep, where the average power and the maximum power of the atoms for various timestep values are shown.

The power dependency with respect to timestep can be seen in FIG. 2, showing the average power and the maximum power of the atoms for various timestep values.

The system used is a ubiquitin protein molecule dissolved in water.

The integrator used is the Velocity Verlet integrator and with a Berendsen type thermostat.

The power is depicted on the vertical axis in au·A$^2$·ps$^{-3}$, au being the unit of atomic mass, A the unit of distance in amstrongs, and ps picoseconds.

The timestep is depicted on the horizontal axis in femtoseconds (1 fs=0.001 ps)

The way of determining these parameters for simulation conditions is to obtain the statistics of the different variables from a short simulation in said conditions. A threshold can be obtained from the maximum of said dynamic variables by inspection.

The threshold will be selected as the maximum plus a margin of 10% of the maximum power value for that system.

Once a threshold for a type of system (gases, fluids, nano-devices, biomolecules) in temperature and pressure conditions is determined, this will be used for similar systems and conditions for one and the same simulator.

The first iterations of the dynamics can be used as a threshold initialization step, automating the process.

Figure 3:
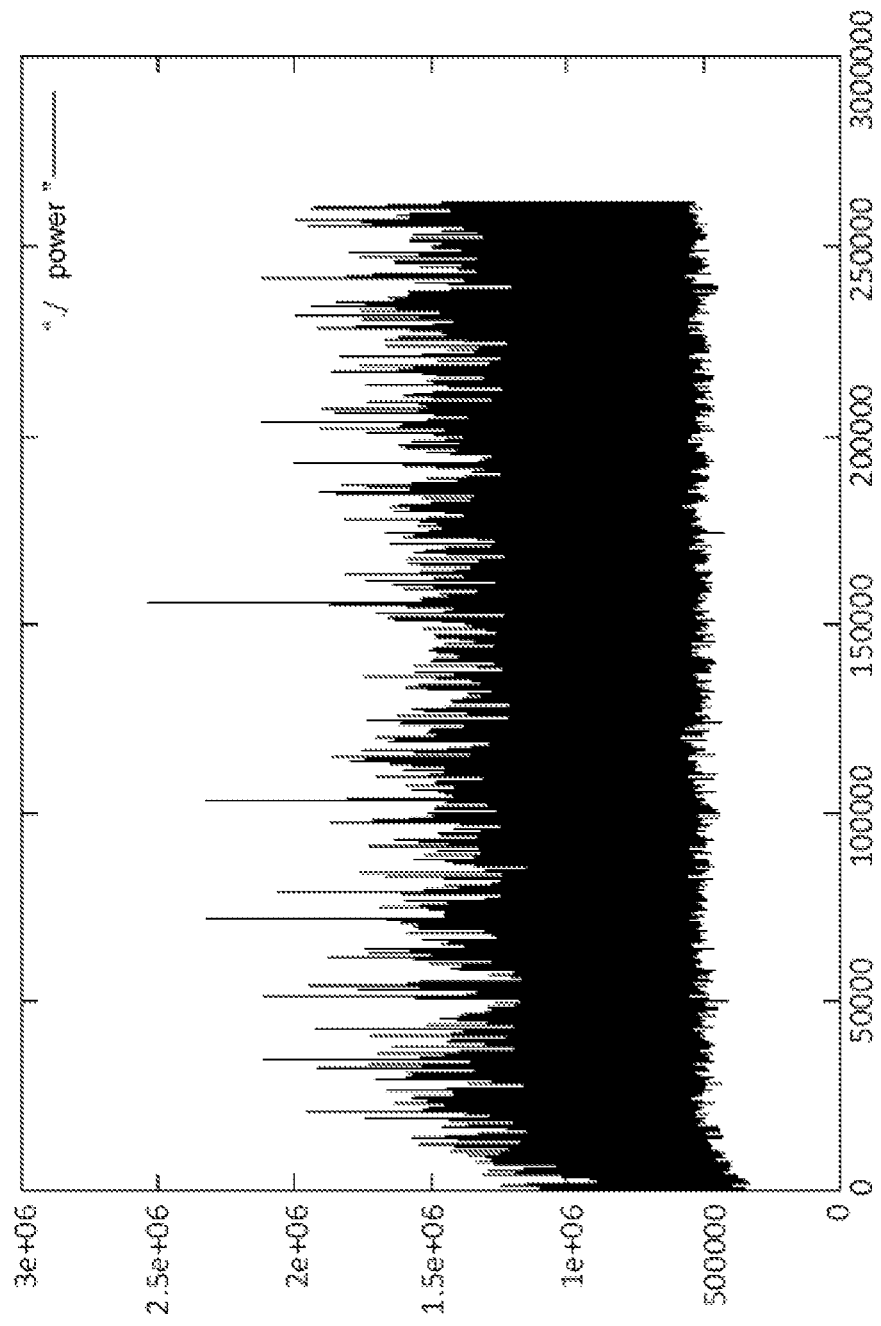
FIG. 3 shows a graph where $p_i$ for the first 260000 iterations of ubiquitin protein simulation is observed, the integration step being 1 femtosecond (1 fs).

$p_i$ for the first 260000 iterations of ubiquitin protein simulation can be seen in FIG. 3, the integration step being 1 femtosecond (1 fs).

It is also the case that the atoms having greater power are hydrogen atoms and they are what generally compromise system stability. An option which has been mentioned above is to increase the mass thereof at the expenses of heavy atoms to which they are bound.

Once these threshold values are determined, there are several strategies compatible with one another for maintaining power in its normal range, maintaining the simulation stable.

1.—Timestep h Control:

If the power is less than the threshold, the system is stable and it is possible to increase the timestep.

If the power is greater, the system enters the instability zone and the timestep must be reduced in order to recover same.

A simple algorithm based on this principle is the following.
In each iteration:
If variable <threshold then h=a·h
If not, then h=b·h
With a>1 and b<1, positive real numbers.

It is convenient to choose b<1/a (conservative condition), such that the system can be stabilized.

This type of control is complemented, when appropriate, with returns to prior steps:
In each iteration:
If variable <threshold then h=a·h
If not, then h=b·h if variable >>threshold then a new state i=state i-k
end if
end if
k being an integer.

In practice with the criterion presented herein, the return to a prior step is only necessary when an excessively large threshold is chosen.

Such algorithms have already been proven for molecular dynamics based on a different criterion, energy conservation (see S. J. Stuart, J. M. Hicks, M. T. Mury, *An Iterative Variable-Timestep Algorithm for Molecular Dynamics Simulations*).

This control can be performed starting from any of the pairs (variable, threshold) based on power:

$$(p_i, u) \tag{15}$$

$$(P_i, U) \tag{16}$$

$$(\Delta p_i, \delta) \tag{17}$$

$$(\Delta P_i, \Delta) \tag{18}$$

Of the 4 pairs, the suggested pair is $(p_i, u)$ because it allows finer power control which results in greater gain.

Figure 4:
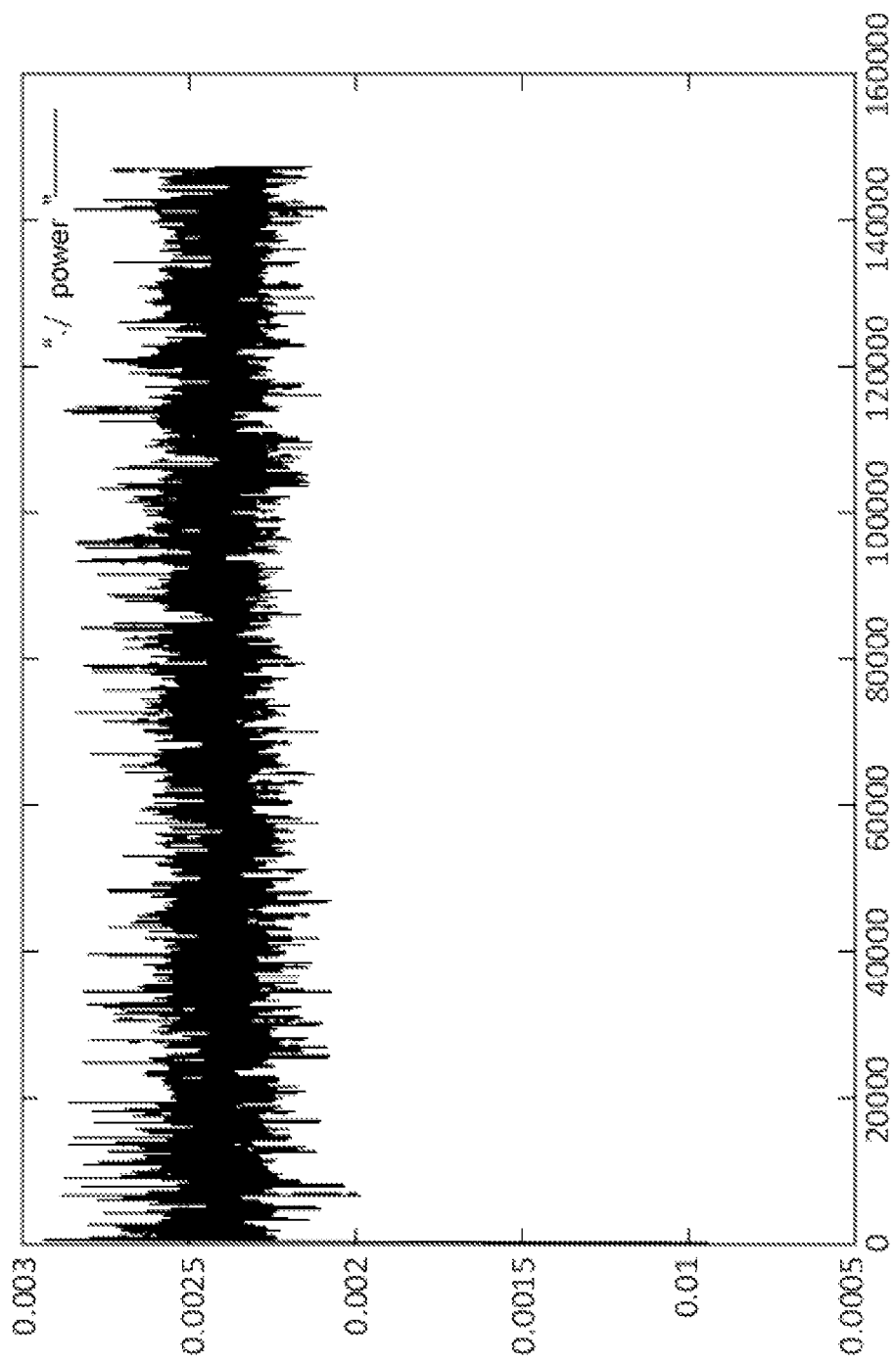
FIG. 4 shows a graph of the evolution of the timestep (in picoseconds) for a type of control with a threshold of 6000000 au·A²·ps⁻³.

Next, FIG. 4 shows the evolution of the timestep (in picoseconds) for such control with a threshold of 6000000 au·A$^2$·ps$^{-3}$ The power dependency and therefore the recommendable threshold dependency with respect to timestep of the simulation is once again seen.

It must be pointed out that a simulation at 2.5 femtoseconds (0.0025 ps) without power control would be unstable, so this method allows extending the timestep.

The advantage of this power control-based adaptive control is that it allows more gain.

Figure 5:
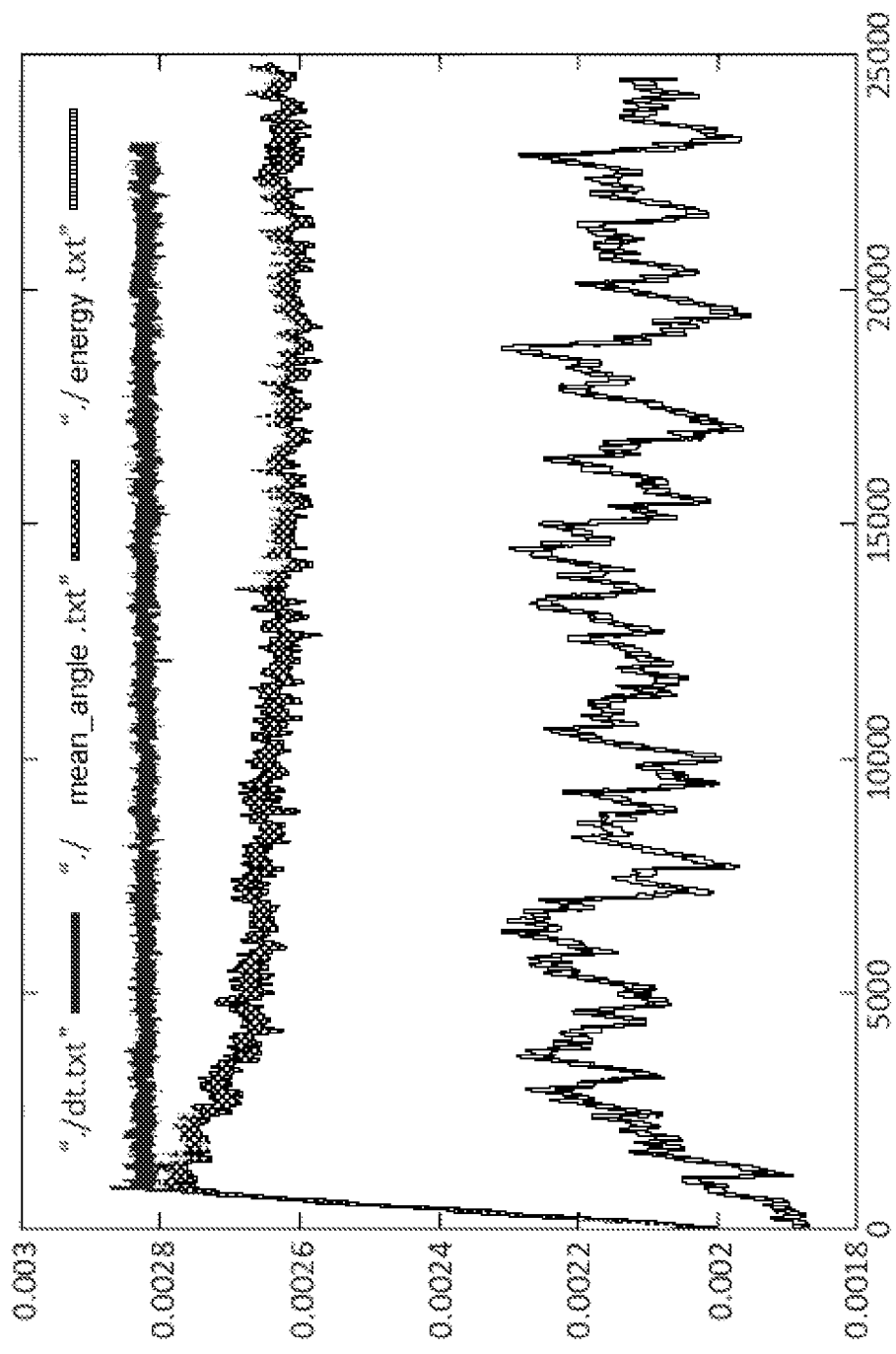
FIG. 5 shows a graph of the timestep behavior for 3 simulations with 3 different criteria for controlling the timestep (in picoseconds). An energy conservation-based control, an aforementioned criterion, is in blue. Another criterion, the alignment between position and velocity variation, is in green. The criterion presented herein is in red. A constraint control algorithm has been introduced to allow increasing the timestep.

FIG. 5 shows how the timestep behaves for 3 simulations with 3 different criteria for controlling timestep (in picoseconds).

An energy conservation-based control, an aforementioned criterion, is in blue.

Another criterion, the alignment between position and velocity variation, is in green.

The criterion presented herein is in red.

A constraint control algorithm has been introduced to allow increasing the timestep.

The small timestep variation and the gain with respect to the rest of the criteria is an indication of this being optimum for controlling timestep based on control loops.

2.—Individual Power Control

A way of maintaining the power of each atom within the normal values is by rescaling the velocity of the atom if its power has exceeded the value threshold:

$$\text{If} \tag{19}$$

$$p_i^\alpha > u$$

then $$\vec{v}_i^\alpha = \frac{u}{p_i^\alpha} \vec{v}_i^\alpha$$

$p_i^\alpha$ and $\vec{v}_i^\alpha$ being the power and velocity of the atom α in the iteration I, respectively.

This problematic atom power correction allows increasing the timestep artificially.

This together with the adaptive control of the timestep allows obtaining even greater timestep values.

Figure 6:
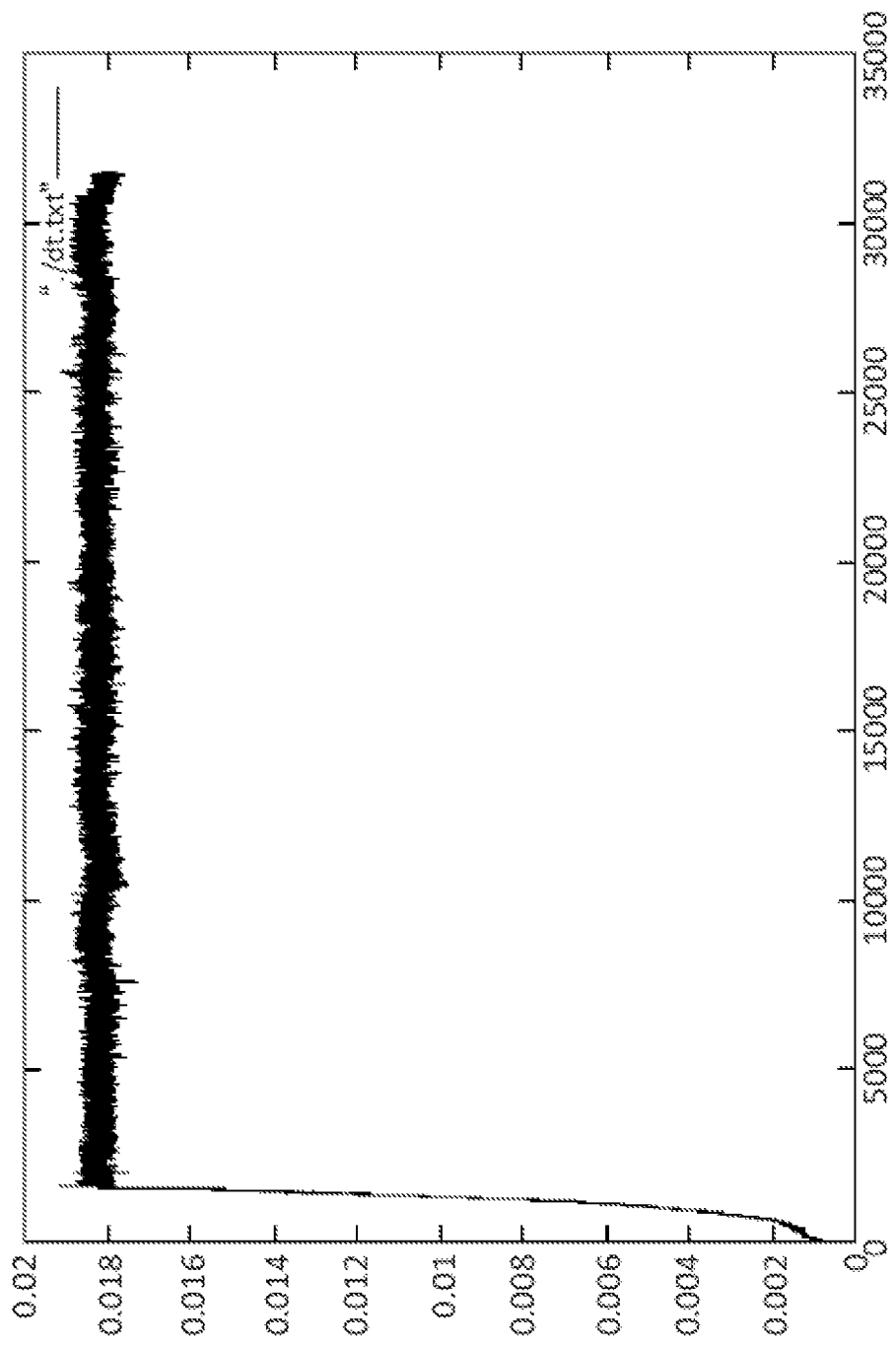
FIG. 6 shows a graph of the combination with constraint algorithms (WIGGLE) and hydrogen atom mass distribution. The timestep in each iteration is shown in the graph in picoseconds.

Along with constraint algorithms (WIGGLE) and hydrogen atom mass distribution, this allows values greater than 18 femtoseconds, as can be observed in FIG. 6 showing the timestep in each iteration (in picoseconds):

3.—Itemizing by Forces

It is possible to itemize these variables for each type of force or group of forces.

Therefore, the power due to the type of force or to the group of forces k in the iteration i for the atom α is:

$$p_i^{\alpha,k} = \vec{F}_i^{\alpha,k} \cdot v_i^{\alpha} \quad (20)$$

$\vec{F}_i^{\alpha,k}$ being the sum of the total force acting on the atom α type of force or the group of forces k.

Similarly, it is possible to define the rest of the variables and thresholds.

This can be itemized for each type of force, for example Van Der Waals, angles; or by groups of forces, for example bound, unbound.

This separation by forces allows controlling the timestep independently for a multiple-timestep (MTS) integration, such as the case of RESPA, where the different timesteps are integrated at a different rate, following a criterion identical to that described in the first section.

All these algorithms allow increasing the timestep by maintaining simulation stability.

As mentioned, the choice of the threshold will depend on the simulation conditions.

In some very conservative conditions, without using constraints or hydrogen mass redistribution and using BBK as an integrator at a temperature of 300 K, the stable timestep is 1.1 fs for a system formed by a ubiquitin-like protein, DHFR (dihydrofolate reductase) dissolved in water.

Given that neither constraints nor hydrogen mass redistribution is used, these atoms are what cause integration problems.

For each simulation step, the power control limits the velocity of the atoms according to equation (19).

It is possible to obtain a timestep of 2.1 fs with this power control without modifying the global dynamics, the gain being 90% with respect to a conventional BBK in the same conditions.

In this case the chosen threshold was 3100000 au·A²·ps⁻³, which is consistent with the values obtained for ubiquitin, a very similar system, at 1 fs.

Given that the dynamics behavior of certain atoms can be very different, it is possible to use a different threshold for each atom If (21)

$$p_i^{\alpha} > u^{\alpha}$$

then $$\vec{v}_i^{\alpha} = \frac{u^{\alpha}}{p_i^{\alpha}} \vec{v}_i^{\alpha}$$

Like hydrogens, the mass of one atom may typically vary greatly with respect to another atom, so said threshold can simply be a function of the mass of each atom.

If (22)

$$p_i^{\alpha} > um^{\alpha}$$

then $$\vec{v}_i^{\alpha} = \frac{um^{\alpha}}{p_i^{\alpha}} \vec{v}_i^{\alpha}$$

The stable timesteps are less than those for the preceding integrator, Verlet velocity and Berendsen thermostat, due particularly to the thermostat, since Berendsen re-scales the velocities, which therefore limits them, but damps the global dynamics. In contrast, BBK uses a Langevin type thermostat, which further reproduces the thermodynamic conditions to be simulated more accurately.

If a threshold by type of force or type of atom is to be used, the way of determining it is similar to that of determining a single threshold. The corresponding behavior of the corresponding power for a very conservative timestep simulation is studied, and the maximum plus a margin is taken.

The invention claimed is:

1. A computer-implemented method for simulating systems of atoms by means of molecular dynamics, which comprises the use of at least one numerical integrator for integrating equations of motion of the atoms, the computer-implemented method comprising:
    controlling a power of at least part of the atoms by carrying out a power control loop that calculates the power of at least part of the atoms to provide a calculated power, and
    wherein a timestep of the at least one numerical integrator is adaptively modified depending on the calculated power of the atoms,
    wherein if the calculated power is less than a lower threshold of a predefined stability power range, the timestep of the at least one numerical integrator is increased, and
    wherein if the calculated power is greater than an upper threshold of the predefined stability power range, the timestep of the integrator is reduced;
    maintaining the power of at least part of the atoms within the predefined stability power range within which the simulation of the systems is considered stable, and
    integrating the equations of motion of the atoms at the rate marked by the timestep the at least one numerical integrator in each instant of the simulation of the systems to maintain the simulation stability as a result of the power control loop.

2. The computer-implemented method according to claim 1, further comprising reducing a velocity of the atoms when the calculated power is greater than the upper threshold of the predefined stability power range to maintain the simulation stability.

3. The computer-implemented method according to claim 2, wherein reducing the velocity of the atoms is performed by means of scaling the velocity to provide a new power equal to the calculated power of the upper threshold of the predefined stability power range.

4. The computer-implemented method according to claim 1, wherein the upper threshold of the predefined stability power range comprises a hundred times a maximum value of dynamic variables for a constant timestep simulation of 0.5 femtoseconds, and the lower threshold of the predefined stability power range comprises a hundred times the minimum value of the dynamic variables.

5. The computer-implemented method according to claim 1, wherein the power of the at least part of the atoms is calculated as a scalar product of a velocity times a force acting thereon.

6. The computer-implemented method according to claim 1, further comprising utilizing constraint algorithms and hydrogen atom mass distribution.

7. The computer-implemented method according to claim 1, wherein the power of at least part of the atoms is maintained within the predefined stability power range two or more predefined stability power ranges, each of which is associated with a different atom of the atoms.

8. The computer-implemented method according to claim 1, wherein a multiple timestep (MTS) integration is used, each of which is controlled independently.

9. The computer-implemented method according to claim 1, wherein the simulated systems of atoms corresponds with: a gas, a liquid, a nano-device, biomolecules, or proteins.

10. The computer-implemented method according to claim 1, further comprising:
  selecting drugs,
    wherein the simulated systems of atoms corresponds with a biomolecule;
  entering data corresponding to the selected drug; and
  upon completion of the simulation, generating data relating to positions, velocities, energies of the molecules and estimating macroscopic properties of the molecules and validity of the selected drug.

11. A system comprising a processor and a memory, the memory storing computer program instructions for simulating systems of atoms by means of molecular dynamics, which comprises the use of at least one numerical integrator for integrating the equations of motion of the atoms, the computer program instructions when executed by the processor cause the system to perform:
  controlling a power of at least part of the atoms of the system by carrying out a power control loop that calculates the power of at least part of the atoms to provide a calculated power, and
  wherein a timestep of the at least one numerical integrator is adaptively modified depending on the calculated power of the atoms,
  wherein if the calculated power is less than a lower threshold of a predefined stability power range, the timestep of the at least one numerical integrator is increased, and
  wherein if the calculated power is greater than an upper threshold of the predefined stability power range, the timestep of the integrator is reduced;
  maintaining the power of at least part of the atoms within the predefined stability power range within which the simulation of the systems is considered stable, and
  integrating the equations of motion of the atoms at the rate marked by the timestep the at least one numerical integrator in each instant of the simulation of the systems to maintain the simulation stability as a result of the power control loop.

12. The system according to claim 11, wherein the system comprises a data input means and a data output means,
  where said computer program instructions are further executable by the processor to cause the system to perform:
  selecting drugs,
  wherein the simulated systems of atoms corresponds with a biomolecule entering data corresponding to the selected drug; and
  upon completion of the simulation, generating data relating to positions, velocities, energies of the molecules and estimating macroscopic properties of the molecules and validity of the selected drug.

* * * * *